United States Patent [19]

Dracopoli et al.

[11] Patent Number: 5,714,329
[45] Date of Patent: Feb. 3, 1998

[54] METHODS FOR THE DIAGNOSIS OF A GENETIC PREDISPOSITION TO CANCER ASSOCIATED WITH VARIANT CDK4 ALLELE

[75] Inventors: Nicolas Dracopoli, Carlsbad, Calif.; Margaret Tucker, Bethesda; Alisa Goldstein, Rockville, both of Md.

[73] Assignees: Sequana Theraputics, Inc., La Jolla, Calif.; The United States of America, Washington, D.C.

[21] Appl. No.: 564,002

[22] Filed: Nov. 29, 1995

[51] Int. Cl.⁶ .................................................. C12Q 1/68
[52] U.S. Cl. .................... 435/6; 536/23.5; 536/24.31; 536/24.33
[58] Field of Search ............ 435/6, 91.2; 536/23.5, 536/24.31, 24.33

[56] References Cited

U.S. PATENT DOCUMENTS 4,683,195  7/1987  Mullis et al. ............................. 435/6

OTHER PUBLICATIONS

Ewen et al. (1993) *Cell* 73:487–497.
Serrano et al. (1993) *Nature* 366:704–707.
Nancarrow et al. (1992) *Genomics* 14:939–947.
Kamb et al. (1994) *Nature Genetics* 8:22–26.
Okamoto et al. (1994) *P.N.A.S.* 91:11045–11049.
Khatib et al. (1993) *Cancer Res.* 53:5535–5541.
Gruis et al. (1995) *Melanoma Res.* 5:169–177.
Liu et al. (1995) *Oncogene* 11:405–412.
Hussussian et al. (1994) *Nature Genetics* 8:15–21.
Nobori et al. (1994) *Nature* 368:753–756.
Wölfel et al. (1995) *Science* 269:1281–1284.
Ladanyi et al. (1995) *J. Pathol.* 175:211–217.
Xiong et al. (1993) *Genes Dev.* 7:1572–1583.
Medema et al. (1995) *P.N.A.S.* 92:6289–6293.

*Primary Examiner*—Scott W. Houtteman
*Attorney, Agent, or Firm*—Pamela Sherwood; Bozicevic & Reed, LLP

[57] ABSTRACT

Protein complexes consisting of a cyclin dependent kinase CDK4 and cyclin D control passage through the G1 checkpoint of the cell cycle by phosphorylating the retinoblastoma protein. The ability of these complexes to phosphorylate RB is inhibited by a family of low molecular weight proteins, including p16, p15 and p18. Germline mutations in the p16 gene have been identified in approximately half of families with hereditary A mutation is described in CDK4 in two unrelated melanoma families that do not carry germline p16 mutations. This CDK4-R24C mutation was detected in 11/11 melanoma patients, 2/17 unaffecteds and 0/5 spouses. This mutation has a specific effect of the p16 binding domain of CDK4, but has no effect on its ability to bind cyclin D and form a functional kinase. Therefore, the germline R24C mutation in CDK4 generates a dominant oncogene that is resistant to normal physiological inhibition by p16.

12 Claims, 2 Drawing Sheets

342

2905

METHODS FOR THE DIAGNOSIS OF A GENETIC PREDISPOSITION TO CANCER ASSOCIATED WITH VARIANT CDK4 ALLELE

This invention was made with Government support. The Government has certain rights in this invention.

INTRODUCTION

1. Technical Field

The field of this invention is diagnosis of a genetic predisposition to cancer.

2. Background

The incidence of melanoma is rapidly increasing in the United States, having tripled in the last 40 years. There are over 18,000 new cases diagnosed every year, out of which 30% will die from the disease. The disease commonly strikes those aged 30 to 50. Caucasians are at a 12-fold greater risk for melanoma than African-Americans. If therapy is initiated in the early stages of disease, melanoma can be effectively treated. The survival rate decreases significantly in the later stages of the disease, particularly after metastasis. Preventive measures, such as avoiding overexposure to the sun, and early detection of lesions, are important tools in management of the disease.

Large families of oncogenes have been described. As a group they provide a representative cross-section of the molecules involved in the control of cellular signaling and proliferation. The tumor suppressor genes have been more difficult to identify than oncogenes, as they are notable primarily in their absence. Tumor suppressors are also closely linked to the control of cell division. It is generally accepted that tumors arise as the result of abnormalities in the expression of oncogenes and/or tumor suppressor genes. A "two-hit model" suggests that malignancies arise when a suppressor is lost, and an oncogene is inappropriately activated. Familial predisposition to cancer may occur when there is a mutation that causes one of these "hits" to be present in the germline DNA of an individual.

A family of protein kinases known as the cyclin dependent kinases (CDKs) regulate the division cycle of eukaryotic cells, and are involved in the loss of division cycle regulation in tumor cells. An orderly progression through the cell cycle requires the sequential activation of individual members of this family, and their consequent phosphorylation of critical substrates. Cell cycle arrest at the G1 checkpoint allows completion of critical macromolecular events prior to S phase. The complexes formed by cyclin dependent kinase 4 (CDK4) and the D-type cyclins have been strongly implicated in the control of cell proliferation during the G1 phase.

CDK4 forms a multiprotein complex with cyclin D, proliferating cell nuclear antigent and p21 protein. These complexes control passage through the G1 checkpoint by phosphorylating the retinoblastoma protein (RB), a tumor suppressor. CDK4 associates separately with p16$^{INK4a}$, particularly in cells lacking a functional retinoblastoma protein. p16$^{INK4a}$ (sometimes referred to as CDKN2 or p16) is also a tumor suppressor, acting in a regulatory feedback circuit to inhibit the kinase activity of CDK4, thereby preventing the cell from cycling.

Cytogenetic abnormalities of chromosome 9p21 are characteristic of malignant melanomas, gliomas, lung cancers and leukaemias. The most frequently deleted region on 9p21 contains the coding region for the CDK4 inhibitor, p16$^{INK4a}$. Numerous sporadic melanomas, gliomas, lung cancers and leukaemias have an absence of detectable p16$^{INK4a}$ gene transcripts. It is estimated that 5 to 12% of melanoma cases are familial, while the remainder are sporadic. Familial melanoma is a genetically heterogeneous disease, and approximately half of the cases show evidence of linkage to the p16$^{INK4a}$ gene. The genetic basis for the predisposition in the remaining half is unknown.

Advances in recombinant DNA technology provide the means to extensively analyze individual genotypes. Information concerning a genetic predisposition to disease may be important in terms of preventive medicine and early diagnosis. Genetic polymorphisms that confer a high susceptibility to disease are therefore of particular interest.

Relevant Literature

Ewen et al. (1993) *Cell* 73:487-497 describe the functional interaction of RB with D-type cyclins. Growth suppression by p16$^{INK4a}$ and RB is described in Medema et al. (1995) *P.N.A.S.* 92:6289-6293.

The subunit rearrangement of cyclin-dependent kinases in transformed cells is described in Xiong et al. (1993) *Genes Dev.* 7:1572-1583. Amplification of CDK4 in human tumors is described in Khatib et al. (1993) *Cancer Res.* 53:5535-5541; and Ladanyi et al. (1995) *J. Pathol.* 175:211-217. Description of a dominant somatic mutation in the CDK4 gene (R24C) may be found in Wölfel et al. (1995) *Science* 269:1281-1284. Deletion of p16$^{INK4a}$ in multiple human cancers is described in Nobori et al. (1994) *Nature* 368:753-756. The association of germline p16$^{INK4a}$ mutations with inherited melanoma is described in Hussussian et al. (1994) *Nature Genetics* 8:15-21; Liu et al. (1995) *Oncogene* 11:405-412; and Gruis et al. (1995) *Melanoma Res.* 5:169-177.

A large number of articles have been published that teach various methods of genetic mapping and mutation analysis. Of particular note are Risch (1990) *Am. J. Hum, Gen.* 46:242-253; Schwengel et al. (1994) *Genomics* 22:46-54; Reed et al. (1994) *Nature Genet.* 7:390-395; Lander & Botstein (1989) *Genetics* 121:185-199; Risch (1991) *Am. J. Hum. Genet.* 48:1058-1064; and Orita et al. (1989) *Genomics* 8:874-879.

SUMMARY OF THE INVENTION

Methods are provided for diagnosing a predisposition to human cancers which are associated with a germline mutation in the CDK4 gene. The mutation is a dominant phenotype, where a single copy of the altered gene causes a predisposition to cancer. Diagnosis is performed by analysis of the CDK4 gene sequence in an individual. Predisposing mutations of interest decrease the ability of CDK4 to be inhibited by its normal inhibitors. These mutations are particularly associated with familial melanoma.

DATABASE REFERENCES FOR DNA SEQUENCES

Figure 1:
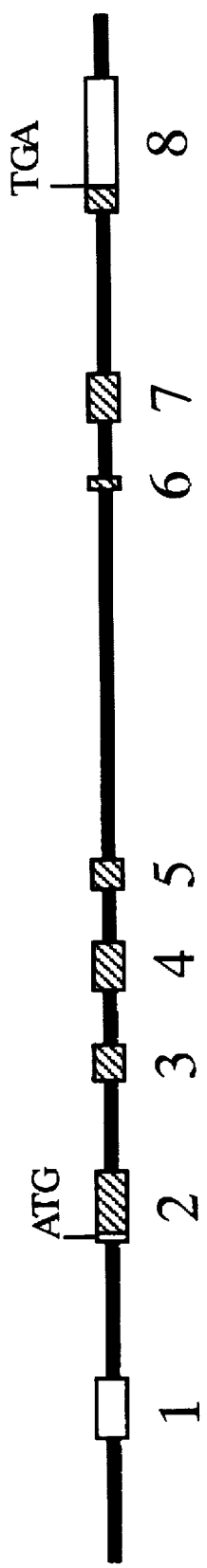
FIG. 1 shows the organization of the CDK4 gene. Open boxes represent the 5' and 3' noncoding region and the filled boxes represent coding regions.

The complete genomic sequence of human CDK4 has the Genbank accession number U37022. The sequence of human CDK4 mRNA has the Genbank accession number M14505. The complete sequence of human p16$^{INK4a}$ mRNA has the Gembank accession number L27211.

DESCRIPTION OF THE SPECIFIC EMBODIMENTS

Methods and compositions are provided for diagnosing a predisposition to human cancers. The methods comprise an analysis of germline DNA for a predisposing mutation in the gene encoding the cyclin-dependent kinase CDK4, where presence of the altered gene confers an increased susceptibility to cancer. Predisposing mutations decrease the ability of CDK4 to be inhibited by its normal inhibitor proteins, e.g. p15, p18, p27, p21 and p16$^{INK4a}$, either through overexpression of CDK4 or through alterations in the CDK4 binding sites. Diagnosis of familial melanoma is of particular interest.

Individuals are screened by analyzing their germline CDK4 gene sequence for the presence of a predisposing mutation, as compared to a normal CDK4 sequence. A "normal" sequence of CDK4 mRNA, and the complete CDK4 gene sequence may be accessed through Genbank, as referenced above. The normal CDK4 sequence shall be understood to include sequence variants in non-coding regions that do not affect the level of expression of the gene, and coding region variants that do not change the amino acid sequence, e.g. "third position" changes.

Predisposing mutations are those changes in the CDK4 DNA sequence that confer an increased susceptibility to cancer. These mutations generally result in a decreased ability of CDK4 to bind and/or be inhibited by its normal inhibitors, e.g. p15, p18, p27, p21 and p16$^{INK4a}$. Such mutations may occur in the control regions of the gene, where expression of CDK4 is upregulated. Alternatively, the mutations will be found in the coding region of the gene, and will alter the amino acid sequence of the protein, particularly the inhibitor binding site. Of particular interest are mutations in the second exon of CDK4 that decrease binding of p16$^{INK4a}$. In one embodiment of the invention, the predisposing mutation is at nucleotide 297 of the CDK4 gene (based on Genbank accession number M14505), resulting in an amino acid change at residue 24 of the mature protein. It is found that an R-to-C transition at this position causes a genetic predisposition to melanoma.

The effect of a sequence variation on CDK4 expression or function is determined by kindred analysis for segregation of the sequence variation with the disease phenotype, e.g. melanoma, glioma, sarcoma, etc. A predisposing mutation will segregate with incidence of the disease. The subject mutations generally have a dominant phenotype, where a single altered allele will confer disease susceptibility. The penetrance will vary with the specific mutation, but may be as high as about 90%.

As an alternative to kindred studies, biochemical studies are performed to determine whether a candidate sequence variation in the CDK4 coding region or control regions affects the quantity or function of the protein. For example, a change in the promoter or enhancer sequence that upregulates expression of CDK4 will cause a disease predisposition. Expression levels of a candidate variant allele are compared to expression levels of the normal allele by various methods known in the art. Methods for determining promoter or enhancer strength include quantitation of the expressed natural protein; insertion of the variant control element into a vector with a reporter gene such as β-galactosidase, chloramphenical acetyltransferase, etc. that provides for convenient quantitation; and the like.

The effect of a sequence variation on the interaction between CDK4 and its normal inhibitors is determined by binding studies or kinase assays, where a decreased level of inhibition or binding is indicative of a predisposing mutation. For example, the variant CDK4 protein may be expressed by conventional recombinant methods, and combined with similarly expressed cyclin D1 and one or more inhibitors, e.g. p15, p18, p21, p27 or p16$^{INK4a}$. The DNA sequences of p15, p18, p16$^{INK4a}$, p21, p27 and cyclin D1 can be accessed through Genbank. Conveniently, one or more of the proteins will be conjugated to a detectable label, e.g. $^{35}$S-methionine, $^3$H-amino acids, fluorescein isothiocyanate, etc. The proteins may be present in the form of cell lysates, or partially purified or purified preparations. The normal CDK4 protein will form stable complexes with cyclin D1 and one or more of the inhibitors. Variant CDK4 having a predisposing mutation will show decreased inhibitor complex formation. The presence of complexes is detected by immunoprecipitation with antibodies specific for any one of the protein components, usually anti-CDK4 antibodies, followed by gel electrophoresis and detection of the specific bands corresponding to each protein. The absence of one of the proteins in the complex indicates decreased binding to CDK4.

Normal CDK4 will phosphorylate retinoblastoma protein (RB) in the presence of cyclin D1. The CDK4 inhibitors decrease the rate of phosphorylation. CDK4 protein expressed from a candidate predisposing sequence is combined in a kinase assay with cyclin D1, RB, and one or more of the inhibitors. A loss of inhibition by a variant CDK4 allele indicates a predisposing mutation.

A number of methods are used for determining the presence of a predisposing mutation in an individual. Genomic DNA is isolated from the individual or individuals that are to be tested. DNA can be isolated from any nucleated cellular source such as blood, hair shafts, saliva, mucous, biopsy, feces, etc. Methods using PCR amplification can be performed on the DNA from a single cell, although it is convenient to use at least about 10$^5$ cells. Generally samples will not include cells suspected of being transformed, e.g. cell lines, tumor biopsies, etc.

A number of methods are available for analyzing genomic DNA sequences. Where large amounts of DNA are available, the genomic DNA is used directly. Alternatively, the region of interest is cloned into a suitable vector and grown in sufficient quantity for analysis, or amplified by conventional techniques. Of particular interest is the use of the polymerase chain reaction (PCR) to amplify the DNA that lies between two specific primers. The use of the polymerase chain reaction is described in Saiki, et al. (1985) Science 239:487, and a review of current techniques may be found in Sambrook, et al. Molecular Cloning: A Laboratory Manual, CSH Press 1989, pp.14.2-14.33.

A detectable label may be included in the amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^3$H; etc. The label may be a two stage system, where the amplified DNA is conjugated to biotin, haptens, etc. having a high afifnity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

Primer pairs are selected from the CDK4 genomic sequence using conventional criteria for selection. The primers in a pair will hybridize to opposite strands, and will collectively flank the region of interest. The primers will hybridize to the complementary sequence under stringent conditions, and will generally be at least about 16 nt in length. Alternatively, the primer pairs SEQ ID NO:15 to SEQ ID NO:30 are used to amplify the specific exons, as shown in the examples. The primers will be selected to amplify the specific region of the CDK4 gene suspected of containing the predisposing mutation. Multiplex amplification may be performed in which several sets of primers are combined in the same reaction tube, in order to analyze multiple exons simultaneously. Each primer may be conjugated to a different label. In one embodiment of the invention, SEQ ID NO:15 and SEQ ID NO:16 are used as the amplification primers to amplify the region containing nucleotide 297.

The amplified or cloned fragment may be sequenced by dideoxy or other methods, and the sequence of bases compared to the normal CDK4 sequence. Alternatively, where the predisposing mutation creates or destroys a recognition site for a restriction endonuclease, the fragment is digested with that endonuclease, and the products size fractionated to determine whether the fragment was digested. Fractionation is performed by gel electrophoresis, particularly acrylamide or agarose gels. Hybridization with the variant sequence may also be used to determine its presence, by Southern blots, dot blots, etc. Single strand conformational polymorphism (SSCP) analysis, denaturing gradient gel electrophoresis (DGGE), and heteroduplex analysis in gel matrices is used to detect conformational changes created by DNA sequence variation as alterations in electrophoretic mobility. The hybridization pattern of a control and variant sequence to an array of oligonucleotide probes immobilised on a solid support, as described in WO 9511995, may also be used as a means of detecting the presence of variant sequences.

The presence of a predisposing mutation is indicative that an individual is at increased risk of developing cancer. From the current data, 80% of the persons that are carriers for the R24C mutation will develop melanoma in their lifetime. Tumors associated with alterations in the CDK4/p16$^{INK4a}$ control of cell cycle include lymphomas, e.g. acute myelogenous lymphomas, acute lymphocytic lymphomas, chronic myelogenous lymphomas, chronic lymphocytic lymphomas, non-Hodgkin's lymphoma, adult T cell leukemia, mixed lineage leukemia; gliomas; sarcomas, e.g. Ewing's sarcoma; carcinomas, e.g. bladder carcinomas, nasopharyngeal carcinomas, pancreatic adenocarcinoma, non-small cell lung carcinomas, eosophagus squamous cancer; peripheral neuroectodermal tumor; mesotheliomas; and Wilms tumor. Of particular interest are tumors known to be associated with alterations in the level or function of CDK4, e.g. Wilms tumor, Ewing's sarcoma, and familial melanoma.

The diagnosis of a disease predisposition allows the affected individual to seek early treatment of potential lesions, and to avoid activities that increase risk for the particular tumor type, e.g. excessive sun exposure and melanoma, smoking and SCLC, etc.

A kit may be provided for practice of the subject methods. Such a kit will contain at least one set of specific primers useful for amplifying a region of the CDK4 gene. In one embodiment of the invention, SEQ ID NO:15 and SEQ ID NO:16 will be used as the primers. Also included may be a restriction endonuclease capable of differentiating between the normal allele, and one with a predisposing mutation.

The following examples are offered by way of illustration and not by way of limitation.

EXPERIMENTAL

Methodology

Subjects. The 10 melanoma families from the National Cancer Institute (342, 372, 377, 909, 928, 2209, 2482, 2851, 2905, 2947) have been described previously (Hussusian et al. supra.; Goldstein et al. (1994) Am. J. Hum. Genet. 54:489–496; and Goldstein et al. (1993) Am. J. Hum. Genet. 52:537–550). Eight families from the Queensland Institute of Medical Research (40138, 40139, 40449, 40566, 40575, 40800, 40870 and 40928) have been described previously (Nancarrow et al. (1993) Am. J. Hum. Genet. 53:936–942; Walker et al. (1995) Hum. Mol. Genet.)

SSCP Methods. The intron-exon boundaries of CDK4 are shown in Table 1. PCR primers flanking the splice sites and coding regions for exons 3–7 were developed for the SSCP analysis, shown in Table 2. Two overlapping PCR assays were developed for exon 2, so that no product exceeded 250 bp. PCR primers for exon 8 were selected from intro 7 and the 3'-untranslated region, so that the entire coding region was contained between the primers. All PCR primers described in Table 2 have a Tm between 58° C.–61° C. PCR was carried out as described in Hussussian et al., supra. for all the 8 primer pairs with an annealling temperature of 55° C., and with the PCR buffer supplemented with 5% DMSO. SSCP was carried out using $^{32}$P-labeled primers, or by separation on 20% non-denaturing gels and silver staining using the PhastSystem apparatus (Pharmacia Biotech).

TABLE 1

Nucleic Acid Residues Surrounding the Intron-Exon Boundaries of CDK4

| Exon | Size (bp) | Splice Acceptor | Splice Donor | Intron (bp) |
|---|---|---|---|---|
| 1 | 207 | | [SEQ ID NO: 1]<br>CTGGCGTGAGgtaagtgCag | 437 |
| 2 | 237 | [SEQ ID NO: 2]<br>gtgattgtagGGTCTCCCTT | [SEQ ID NO: 3]<br>ATGTTGTCCGgtgagaaggt | 157 |
| 3 | 136 | [SEQ ID NO: 4]<br>ctctggtcagGCTGATGGAC | [SEQ ID NO: 5]<br>AACGATCAAGgtgagtgggg | 117 |
| 4 | 168 | [SEQ ID NO: 6]<br>ttgaaactagGATCTGATGC | [SEQ ID NO: 7]<br>TACACCCGTGgtcagtagaa | 157 |

TABLE 1-continued

Nucleic Acid Residues Surrounding the Intron-Exon Boundaries of CDK4

| Exon | Size (bp) | Splice Acceptor | Splice Donor | Intron (bp) |
|---|---|---|---|---|
| 5 | 110 | [SEQ ID NO: 8] ttccctttagGTTGTTACAC | [SEQ ID NO: 9] TTCGTCGAAAgtatgggacc | 1138 |
| 6 | 51 | [SEQ ID NO: 10] ctcaccttagGCCTCTCTTC | [SEQ ID NO: 11] AAATCTTTGAgtaagtgacc | 135 |
| 7 | 136 | [SEQ ID NO: 12] tcccccacagCCTGATTGGG | [SEQ ID NO: 13] GCTGCTGCTGgtaactggag | 565 |
| 8 | 398 | [SEQ ID NO: 14] ctcccctcagGAAATGCTGA | | |

TABLE 2

PCR Primers for SSCP Analysis of 7 Coding Exons from CDK4

| Exon | Size | Forward Primer (5'-3') | Reverse Primer (5'-3') |
|---|---|---|---|
| 2A | 197 | [SEQ ID NO: 15] GCTGCAGGTCATACCATCCT | [SEQ ID NO: 16] CTCTCACACTCTTGAGGGCC |
| 2B | 222 | [SEQ ID NO: 17] CCCGTGATCCCCACAGT | [SEQ ID NO: 18] ATCATCACACCCCACCTATAGG |
| 3 | 222 | [SEQ ID NO: 19] GAGAGGCCATGTTGGGTTAA | [SEQ ID NO: 20] TCCACCTCTCAATGCCTACC |
| 4 | 231 | [SEQ ID NO: 21] TTCCAGTGCATCTGTACCTCC | [SEQ ID NO: 22] CCCATTTTGGTACCATCTTTC |
| 5 | 219 | [SEQ ID NO: 23] GTGTTTCATGGTAACCCATGG | [SEQ ID NO: 24] TTTATGAACAAGCGATTTGGG |
| 6 | 204 | [SEQ ID NO: 25] CCCAAAGTGCTGGAATTGTT | [SEQ ID NO: 26] AAATCTTTTTCTCCCATGTTGG |
| 7 | 205 | [SEQ ID NO: 27] AGGACCCTCCTGACCAGAGT | [SEQ ID NO: 28] CTTTCCCTGTGCCCACAG |
| 8 | 190 | [SEQ ID NO: 29] TCATGGTTTTCTGACCTTTGC | [SEQ ID NO: 30] GCCCTCTCAGTGTCCAGAAG |

DNA Sequencing. The 12 kb clone containing CDK4 was sonicated and treated with Bal31 and further repaired with T4 DNA polymerase. DNA fragments 0.8–1.5 kb were ligated into the SmaI site of M14mp9. Inserts were amplified by PCR and sequenced from both orientations with dye-labeled primers (M13-21 and M13RP) on an ABI 373 automated sequencer (Applied BioSystems, Foster City Calif.). Sequenced fragments were assembled using the ABI autoassembler.

Results

The intron/exon boundaries of CDK4 were determined by sequencing a genomic clone containing the entire gene, and by comparison with the known cDNA sequence. The CDK4 gene consists of 8 exons within a 5 kb segment, shown in FIG. 1. There is a single 5' untranslated exon. The initiation codon is located in exon 2, and the stop codon and 3' untranslated region are contained in exon 8. The CDK4 gene is located on chromosome 12q13, in a region that is not rearranged or deleted in melanomas. The CDK4 genomic sequence has been deposited in GenBank (Accession number U37022).

Ten families with hereditary melanoma characterized at the National Cancer Institutes were selected for analysis because they did not show evidence of linkage to chromosome 9p21, or did not carry a mutation in p16$^{INK4a}$. SSCP analyses were completed for all CDK4 coding exons on a single affected individual from each of the eleven families. One SSCP variant pattern was detected in assays for exon 2A in two samples from families 342 and 2905. PCR products from these samples were cloned to separate the alleles and sequenced. Analysis of the sample from both families showed an identical C-to-T transition at nucleotide 297 (based on Genbank accession number M14505). This C-to-T transition creates a novel StuI restriction digest of the 198 bp exon 2A PCR product, which generates two fragments of 149 and 49 bp. The C-to-T transition at nucleotide 297 caused the replacement of an arginine (R) with cysteine (C) at position 24, and is designated as R24C.

Figure 2:
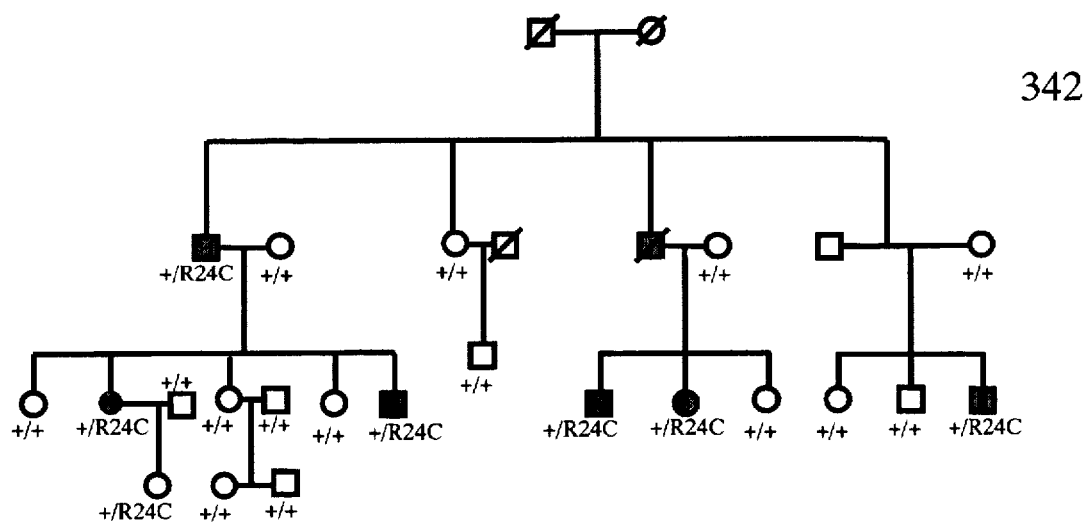
FIG. 2 shows two melanoma kindreds showing segregation of the CDK4-R24C variant. Individuals with melanoma are represented by filled symbols and unaffected family members and spouses are represented by open symbols.
Figure 2:
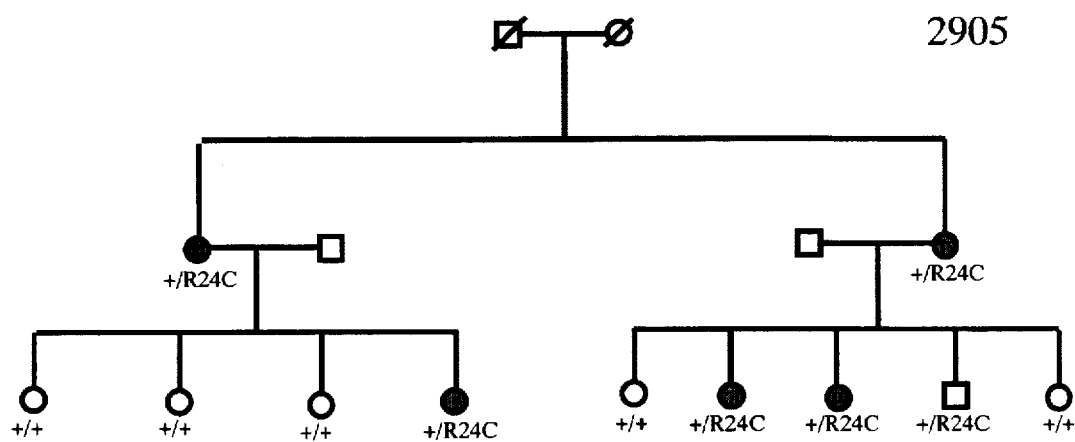

The segregation pattern of the R24C variant in families 342 and 2905 was analyzed by SSCP and StuI restriction analysis, shown in FIG. 2. Each of the 11 melanoma patients in both families carried the R24C variant, and only 2/17 unaffected family members and 0/5 spouses carried this variant. The unaffected carriers (IV-1 in family 342 and (II-8 in family 2905) were only 15 and 30 years old, respectively, when last examined, and may still develop melanoma since the average age of diagnosis in these families is 38 years. In family 342, the unaffected member II-7 is an obligate carrier of the R24C, and is also non-penetrant for the disease. This patient was not clinically examined. Therefore, 11/14 carriers and obligate carriers of the R24C mutation in these two families have melanoma, which suggests a penetrance of 0.8, which is very similar to that described for p16 mutants (Hussussian et al. (1994) *Nature Genetics* 8:15–21). A second set of 21 melanoma families were also screened by StuI digestion for the CDK4-R24C mutation. These 22 families were selected because they did not contain p16 mutations. Two affected members of each family were analyzed, and no additional cases of the CDK4-R24C variant were identified.

The identification of the R24C mutation that segregates with the disease in two apparently unrelated melanoma kindreds provides strong evidence that CDK4 is a second familial melanoma gene. The analysis of p16 and CDK4 in a common set of 19 kindreds has demonstrated p16 mutations in 10 kindreds and CDK4 mutations in two kindreds. The CDK4-R24C protein is resistant to normal inhibition by p16 and is predicted to function as a dominant oncogene. This is in contrast to the more common mutations in p16 observed in familial melanoma that function as a recessive tumor gene, and require deletion or mutation of the wild-type allele. Despite the differences in the mode of action of these two genes, the age of onset, tumor number and pathology are indistinguishable between melanoma families carrying p16 or CDK4 mutations.

The identification of reciprocal patterns of mutation in genes in this pathway is not unprecedented. Analysis of small cell lung carcinoma has identified deletions of p16 in the subset of tumors that do not carry mutations or deletions of the RB gene. Amplification of CDK4 is common in gliomas and sarcomas. Therefore it appears that normal regulation of the G1 checkpoint can be overcome by amplification of the amount of CDK4 protein that overwhelms the normal levels of p16 inhibition, or by mutation of the p16 binding site in CDK4 that prevents normal regulation.

It is evident from the above results that the subject invention provides for means of identifying individuals having a increased risk of developing cancer as a result of germline mutations in the cyclin dependent kinase, CDK4. The diagnosis of this predisposition allows the affected individual to make life style changes appropriate for disease prevention and early detection.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

---

What is claimed is:

1. A method for detecting a hereditary predisposition to cancer in an individual, the method comprising:

analyzing the germ line genomic DNA of said individual for the presence of a CDK4 allele comprising a predisposing mutation, wherein the presence of said predisposing mutation is indicative of an increased susceptibility to cancer.

2. A method according to claim 1, wherein said predisposing mutation causes a decrease in the ability of CDK4 to be inhibited by at least one of its normal inhibitors.

3. A method according to claim 2, wherein said at least one normal inhibitor is $p16^{INK4a}$.

4. A method according to claim 3, wherein said predisposing mutation is in the CDK4 exon 2.

5. A method according to claim 4, wherein said predisposing mutation causes an R to C transition at amino acid 24 of the CDK4 protein.

6. A method according to claim 1, wherein said analyzing the germline genomic sequence comprises the steps of:

amplifying a region of the CDK4 gene from isolated genomic DNA to provide an amplified fragment;

detecting the presence of a variant sequence in said amplified fragment.

7. A method according to claim 6, wherein said detecting step comprises direct sequence analysis.

8. A method according to claim 6, wherein said detecting step comprises hybridization with a probe specific for the sequence of said predisposing mutation.

9. A method according to claim 6, wherein said detecting step comprises digestion with a restriction endonuclease.

10. A method for detecting a hereditary predisposition to familial melanoma in an individual, the method comprising:

analyzing the germline genomic DNA of said individual for the presence of a predisposing mutation resulting in an R to C transition at amino acid 24 of CDK4; wherein the presence of said predisposing mutation is indicative of an increased susceptibility to melanoma.

11. A method according to claim 10, wherein said analyzing the germline genomic sequence comprises the steps of:

amplifying at least a portion of exon 2 of the CDK4 gene from isolated genomic DNA by polymerase chain reaction to provide an amplified fragment;

detecting the presence of a variant sequence at nucleotide 297 of the CDK4 gene in said amplified fragment.

12. A method according to claim 11, wherein said detecting step comprises digestion with StuI restriction endonuclease.

* * * * *

UNITED STATES PATENT AND TRADEMARK OFFICE
CERTIFICATE OF CORRECTION

PATENT NO. : 5,714,329
DATED : February 3, 1998
INVENTOR(S) : Nicolas Dracopoli, Margaret Tucker, Alisa Goldstein It is certified that error appears in the above-identified patent and that said Letters Patent is hereby corrected as shown below:

ABSTRACT

The third sentence should read as follows: Germline mutations in the p16 gene have been identified in approximately half of families with hereditary melanoma.

Signed and Sealed this

Eighth Day of September, 1998

Attest:

BRUCE LEHMAN

Attesting Officer

Commissioner of Patents and Trademarks

SEQUENCE LISTING ( 1 ) GENERAL INFORMATION:

( i i i ) NUMBER OF SEQUENCES: 30

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:1:

CTGGCGTGAG GTAAGTGCAG                                                    2 0

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:2:

GTGATTGTAG GGTCTCCCTT                                                    2 0

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:3:

ATGTTGTCCG GTGAGAAGGT                                                   20

( 2 ) INFORMATION FOR SEQ ID NO:4:

( i ) SEQUENCE CHARACTERISTICS:
         ( A ) LENGTH: 20 base pairs
         ( B ) TYPE: nucleic acid
         ( C ) STRANDEDNESS: single
         ( D ) TOPOLOGY: linear ( i i ) MOLECULE TYPE: other nucleic acid
         ( A ) DESCRIPTION: /desc = "Primer"

( x i ) SEQUENCE DESCRIPTION: SEQ ID NO:4:

CTCTGGTCAG GCTGATGGAC                                                   20

( 2 ) INFORMATION FOR SEQ ID NO:5:

( i ) SEQUENCE CHARACTERISTICS:
         ( A ) LENGTH: 20 base pairs
         ( B ) TYPE: nucleic acid
         ( C ) STRANDEDNESS: single
         ( D ) TOPOLOGY: linear ( i i ) MOLECULE TYPE: other nucleic acid
         ( A ) DESCRIPTION: /desc = "Primer"

( x i ) SEQUENCE DESCRIPTION: SEQ ID NO:5:

AACGATCAAG GTGAGTGGGG                                                   20

( 2 ) INFORMATION FOR SEQ ID NO:6:

( i ) SEQUENCE CHARACTERISTICS:
         ( A ) LENGTH: 20 base pairs
         ( B ) TYPE: nucleic acid
         ( C ) STRANDEDNESS: single
         ( D ) TOPOLOGY: linear ( i i ) MOLECULE TYPE: other nucleic acid
         ( A ) DESCRIPTION: /desc = "Primer"

( x i ) SEQUENCE DESCRIPTION: SEQ ID NO:6:

TTGAAACTAG GATCTGATGC                                                   20

( 2 ) INFORMATION FOR SEQ ID NO:7:

( i ) SEQUENCE CHARACTERISTICS:
         ( A ) LENGTH: 20 base pairs
         ( B ) TYPE: nucleic acid
         ( C ) STRANDEDNESS: single
         ( D ) TOPOLOGY: linear ( i i ) MOLECULE TYPE: other nucleic acid
         ( A ) DESCRIPTION: /desc = "Primer"

( x i ) SEQUENCE DESCRIPTION: SEQ ID NO:7:

TACACCCGTG GTCAGTAGAA                                                   20

( 2 ) INFORMATION FOR SEQ ID NO:8:

( i ) SEQUENCE CHARACTERISTICS:
         ( A ) LENGTH: 20 base pairs
         ( B ) TYPE: nucleic acid
         ( C ) STRANDEDNESS: single
         ( D ) TOPOLOGY: linear ( i i ) MOLECULE TYPE: other nucleic acid
         ( A ) DESCRIPTION: /desc = "Primer"

(x i) SEQUENCE DESCRIPTION: SEQ ID NO:8:

TTCCCTTTAG GTTGTTACAC                    20

(2) INFORMATION FOR SEQ ID NO:9:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Primer"

(x i) SEQUENCE DESCRIPTION: SEQ ID NO:9:

TTCGTCGAAA GTATGGGACC                    20

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Primer"

(x i) SEQUENCE DESCRIPTION: SEQ ID NO:10:

CTCACCTTAG GCCTCTCTTC                    20

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Primer"

(x i) SEQUENCE DESCRIPTION: SEQ ID NO:11:

AAATCTTTGA GTAAGTGACC                    20

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Primer"

(x i) SEQUENCE DESCRIPTION: SEQ ID NO:12:

TCCCCCACAG CCTGATTGGG                    20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Primer"

(x i) SEQUENCE DESCRIPTION: SEQ ID NO:13:

GCTGCTGCTG GTAACTGGAG                                                                20

(2) INFORMATION FOR SEQ ID NO:14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Primer"

(x i) SEQUENCE DESCRIPTION: SEQ ID NO:14:

CTCCCCTCAG GAAATGCTGA                                                                20

(2) INFORMATION FOR SEQ ID NO:15:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Primer"

(x i) SEQUENCE DESCRIPTION: SEQ ID NO:15:

GCTGCAGGTC ATACCATCCT                                                                20

(2) INFORMATION FOR SEQ ID NO:16:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Primer"

(x i) SEQUENCE DESCRIPTION: SEQ ID NO:16:

CTCTCACACT CTTGAGGGCC                                                                20

(2) INFORMATION FOR SEQ ID NO:17:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Primer"

(x i) SEQUENCE DESCRIPTION: SEQ ID NO:17:

CCCGTGATCC CCACAGT                                                                   17

(2) INFORMATION FOR SEQ ID NO:18:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (i i) MOLECULE TYPE: other nucleic acid
        (A) DESCRIPTION: /desc = "Primer"

( x i ) SEQUENCE DESCRIPTION: SEQ ID NO:18:

ATCATCACAC CCCACCTATA GG                                                       22

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:19:

GAGAGGCCAT GTTGGGTTAA                                                          20

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:20:

TCCACCTCTC AATGCCTACC                                                          20

( 2 ) INFORMATION FOR SEQ ID NO:21:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:21:

TTCCAGTGCA TCTGTACCTC C                                                        21

( 2 ) INFORMATION FOR SEQ ID NO:22:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:22:

CCCATTTTGG TACCATCTTT C                                                        21

( 2 ) INFORMATION FOR SEQ ID NO:23:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc = "Primer"

( x i ) SEQUENCE DESCRIPTION: SEQ ID NO:23:

GTGTTTCATG GTAACCCATG G 21

( 2 ) INFORMATION FOR SEQ ID NO:24:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "Primer"

( x i ) SEQUENCE DESCRIPTION: SEQ ID NO:24:

TTTATGAACA AGCGATTTGG G 21

( 2 ) INFORMATION FOR SEQ ID NO:25:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "Primer"

( x i ) SEQUENCE DESCRIPTION: SEQ ID NO:25:

CCCAAAGTGC TGGAATTGTT 20

( 2 ) INFORMATION FOR SEQ ID NO:26:

( i ) SEQUENCE CHARACTERISTICS:
  ( A ) LENGTH: 22 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "Primer"

( x i ) SEQUENCE DESCRIPTION: SEQ ID NO:26:

AAATCTTTTT CTCCCATGTT GG 22

( 2 ) INFORMATION FOR SEQ ID NO:27:

( i ) SEQUENCE CHARACTERISTICS:
  ( A ) LENGTH: 20 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "Primer"

( x i ) SEQUENCE DESCRIPTION: SEQ ID NO:27:

AGGACCCTCC TGACCAGAGT 20

( 2 ) INFORMATION FOR SEQ ID NO:28:

( i ) SEQUENCE CHARACTERISTICS:
  ( A ) LENGTH: 18 base pairs
  ( B ) TYPE: nucleic acid
  ( C ) STRANDEDNESS: single
  ( D ) TOPOLOGY: linear ( i i ) MOLECULE TYPE: other nucleic acid
  ( A ) DESCRIPTION: /desc = "Primer"

(x i) SEQUENCE DESCRIPTION: SEQ ID NO:28:

CTTTCCCTGT GCCCACAG                                                18

(2) INFORMATION FOR SEQ ID NO:29:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(x i) SEQUENCE DESCRIPTION: SEQ ID NO:29:

TCATGGTTTT CTGACCTTTG C                                            21

(2) INFORMATION FOR SEQ ID NO:30:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "Primer"

(x i) SEQUENCE DESCRIPTION: SEQ ID NO:30:

GCCCTCTCAG TGTCCAGAAG                                              20